United States Patent [19]

Burtle et al.

[11] Patent Number: 5,030,657

[45] Date of Patent: Jul. 9, 1991

[54] L-CARNITINE SUPPLEMENTED CATFISH DIET

[75] Inventors: Gary J. Burtle; G. Larry Newton, both of Tifton, Ga.; Stephen A. Blum, Des Moines, Iowa

[73] Assignees: University of Georgia Research Foundation, Inc., Athens, Ga.; Lonza Inc., Fair Lawn, N.J.

[21] Appl. No.: 425,694

[22] Filed: Oct. 23, 1989

[51] Int. Cl.$^5$ ...................... A61K 31/205; A23K 1/18
[52] U.S. Cl. ................................... 514/556; 514/951; 514/963; 426/805
[58] Field of Search ...................... 514/556, 951, 963; 119/3; 426/805

[56] References Cited

FOREIGN PATENT DOCUMENTS 121441 9/1981 Japan .
0126420 8/1982 Japan .

OTHER PUBLICATIONS

Chemical Abstracts, vol. 96:5198n, (1982).
Chemical Abstracts, vol. 106:195127j, (1987).
Garling, D. L., Jr. et al., *Prog. Fish. Cult.* 39(1), 43-47, (1977).
Santulli, A. et al., *J. Fish Biol.* 28, 81-86, (1986).
Santulli, A. et al., *Aquaculture* 59, 177-186 (1986).
H. Randal Robinette, Chapter 7, "Feed Formulation and Process", *Nutrition and Feeding of Channel Catfish* (revised), Southern Cooperative Series Bulletin No. 296, pp. 29-57 (Feb. 1984).
"Nutrition and Feeding of Channel Catfish", edited by R. R. Stickney and R. T. Lovell, Nutritional Subcommittee of USDA Regional Research Project S-83, Southern Cooperative Series Bulletin 218, revised as Southern Regional Cooperative Research Project S-168, pp. 1-28.

*Primary Examiner*—Frederick E. Waddell
*Assistant Examiner*—Kevin Weddington
*Attorney, Agent, or Firm*—Kilpatrick & Cody

[57] ABSTRACT

Fish feed compositions supplemented with up to 0.5% L-carnitine, preferably between 0.01% to 0.3% L-carnitine, produce greater growth gains, decreased fat levels in tissues, and increased resistance to stress (ammonia toxicity) in fish, as compared to fish fed the same diet without supplemental carnitine.

23 Claims, No Drawings

L-CARNITINE SUPPLEMENTED CATFISH DIET

BACKGROUND OF THE INVENTION

This invention generally relates to diet supplements for aquaculture species, especially catfish, for increasing the rate and efficiency of fish growth.

A major function of lipids in modern nutrition is to serve as a substrate for production of metabolic energy. Mechanisms regulating the production of metabolic energy under a wide variety of physiological conditions are required for survival of the species. The critical role of carnitine in the production of energy from long-chain fatty acids is well recognized. Carnitine also has a role in the production of metabolic energy from several substrates in addition to long-chain fatty acids. As a result, adequate carnitine is essential in maintaining health.

Unlike most vitamins and vitamin-like substances, carnitine was identified and synthesized long before the discovery of its nutritional role. Carnitine was first found in muscle extracts by two Russian scientists in 1905, identified as beta-hydroxy-alpha-butyrobetaine, and named from the latin carnis, meaning flesh or meat. In the late 1940's, Fraenkel discovered that carnitine was a required substrate for the mealworm *Tenebrio molitor*. He named it vitamin $B_r$, although it was later established that carnitine is not a vitamin for higher organisms since most of the animal requirement is fulfilled by biosynthesis. Early research literature also calls carnitine vitamin $B_{11}$. In 1959, Fritz found that carnitine stimulated the rate of fat burning (called "beta-oxidation"). Subsequent investigations revealed that the mechanism of carnitine action was the transport of fats by a carnitine-dependent mechanism into the mitochondria where they are utilized for energy.

Carnitine is chemically termed 3-hydroxy-4-N-trimethylamino butyric acid; it is similar to choline and synthesized in animals from amino acids. However, unlike amino acids, carnitine is not used for protein synthesis. Carnitine, like many other biological molecules, comes in two forms: L-carnitine and D-carnitine.

Although these isomers are mirror images of each other, only the L-isomer is biologically active. The D-form is completely inactive, and may even inhibit the utilization of L-carnitine. Whether supplied by the diet or from endogenous synthesis, carnitine is essential in the metabolism and movement of fatty acids within and between cells. An enzyme, carnitine acyltransferase, has been found to be part of the mechanism for releasing CoA and acyl-CoA. The effect of carnitine on fatty acid metabolism seems to be limited to fatty acids with chain lengths greater than $C_8$. Since palmitylcarnitine also stimulates fat synthesis in livers, another vitamin role of carnitine may be in the regulation of lipogenesis.

Most organisms have the ability to produce their own carnitine. The endogenous production of carnitine appears to occur mainly in the liver, and requires two amino acids, lysine and methionine, three vitamins, vitamin $B_3$ (niacin), vitamin $B_6$ and vitamin C (ascorbic acid), and iron. Trimethyl-lysine is produced by methylation of lysine using a methyl group from methionine. The trimethyl-lysine is converted to an aldehyde using PALP as a co-factor, which is oxidized to a butyrate by an NAD-linked dehydrogenase. The butyrate is then hydroxylated by a ketoglutarate-ferrous ascorbate compound to form carnitine.

The role of carnitine in nutrition received little attention until 1973, when the first carnitine-deficient human patient was described. Since then, many clinical investigations have focused on biomedical aspects of carnitine deficiency, as well as on the effects of supplementary dietary carnitine on disease processes. No deficiency problems in normal vertebrates have yet been found under practical conditions. Nevertheless, young rats, chick embryos and rabbits on a low level of nutrition have all been shown to grow more rapidly when carnitine has been supplied directly or indirectly. There have also been reports that supplementation of an adequate diet of young pigs with carnitine may enhance growth.

One important, and as yet unresolved, issue is the relative contribution of diet and biosynthesis to the total carnitine intake. Some animal work, particularly studies conducted on mammals, has been published in this area indicating that biosynthesis of carnitine in adult animals is far more important than diet.

Improving feed efficiency and feed responses is particularly desirable in view of the rising cost of the commodities used to prepare the feeds. Commercial aquaculture, especially of catfish and crustaceans, has grown rapidly over the last several years, yet few improvements in feed composition or efficiency have been made. Channel catfish, for example, are commonly fed diets with 32 to 36% crude protein, with most of the protein in the form of soybean meal and menhaden fish meal. In recent years, fish meal has sometimes been replaced with a combination of soybean meal and meat-bone meal. The increase in plant protein concentrate may cause the diet to be less digestible and perhaps less metabolizable. Fish fed diets of plant material and higher amounts of carbohydrate or fat may develop lipid accumulation in certain tissues, such as the liver and muscle, rather than convert the energy into growth. Garling, D. L. Jr. et al., "Effects of Dietary Carbohydrate-to-Lipid Ratios on Growth and Body Composition of Fingerling Channel Catfish" *Prog. Fish-Cult.* 39(1), 43–47 (1977).

Researchers have investigated several additives for their effect on growth and response to stress in fish. Most of these additives are purified or synthesized forms of vitamins, essential amino acids, and essential fatty acids. Others are digestive aids which include individual enzymes and mixtures of gastric enzymes. Growth or sex hormones have been added to culture water or have been dissolved in acetone prior to coating onto the surface of fish food. In these cases, extra additive is used to compensate for losses from the leaching or diluting effect of water. In one example, in Italy, administration of L-carnitine to the culture water was credited for increasing growth of sea bass fry. Santulli, A. et al., "The Effects of Carnitine on Growth of Sea Bass", *J. Fish Biol.* 28, 81–86 (1986). Santulli, A. et al., in "Supplemental Dietary Carnitine Effects on Growth and Lipid Metabolism of Hatchery-reared Sea Bass (*Dicentrarchus labrax* L.)", *Aquaculture* 59, 177–86 (1986), demonstrated that carnitine containing diets, prepared using a process normally used to incorporate fat soluble hormones rather than water soluble materials, increased specific growth rate and reduced liver and muscle lipid concentrations of sea bass. The diets were prepared by soaking the feed composition in a carnitine solution and drying, to a final concentration of approximately 2.0% L-carnitine by weight of dry feed. The actual amount fed to the fish cannot be ascertained based on the information provided but was less than the 2.0% because of leaching of substantial amounts of the water soluble carnitine into the water.

It is therefore an object of the present invention to provide commercial fish diets containing low doses of L-carnitine which are effective in increasing the rates of weight gain and feed efficiency.

It is a further object of the present invention to provide commercial fish diets which reduce fat in processed fish.

It is a still further object of the present invention to provide commercial fish diets which can be used to increase resistance to stress.

It is another object of the present invention to provide commercial warmwater fish diets which specifically increase resistance to ammonia toxicity.

SUMMARY OF THE INVENTION

Pelletized or extruded commercial fish feeds, especially catfish feeds, containing L-carnitine at levels from 0.005% to 1.0% of the feed dry weight results in fish growth at significantly higher rates than diets with only background amounts of L-carnitine (generally in the range of 0.003% carnitine). The higher L-carnitine diet also reduces fat in the fish tissues and increases resistance to chronic ammonia toxicity. The L-carnitine is preferably administered to catfish in a form containing between approximately 0.01 and 0.3% carnitine by dry weight of feed. Optimum levels of L-carnitine will depend in part on the age of the fish, with smaller fish requiring greater amounts and larger fish requiring lower amounts.

The effectiveness of the L-carnitine supplemented diet in increasing fish growth rates was demonstrated by feeding L-carnitine enhanced diets (at concentrations of 0.05%, 0.1% and 0.2% L-carnitine based on dry weight of feed) to channel catfish fingerlings for twelve weeks. The 0.1% L-carnitine diet showed the highest gain relative to control fish fed a commercial diet. Other examples demonstrate the effectiveness of supplemental L-carnitine in treating ammonia toxicity and in decreasing fat content of visceral tissue.

DETAILED DESCRIPTION OF THE INVENTION

Increases in growth rates, decreases in fat content of visceral tissues and increases in resistance to ammonia toxicity are obtained in fish by increasing the percentage of L-carnitine in the diet to levels greater than those present in commercial feed, from greater than about 0.005% up to approximately 1.0% L-carnitine by dry weight of food. In a preferred embodiment for administration to catfish, between 0.01% and 0.3% L-carnitine is added to a commercial diet in a form that minimizes leaching of the L-carnitine into the water at the time of feeding.

The discovery that carnitine supplementation can improve growth or survival of fish is surprising in view of the studies indicating that biosynthesis of carnitine in adult animals is significantly more important that diet. Since enzyme systems develop as fish mature, very young fish may require more carnitine from dietary sources than older fish. Also, fish growing under stressful conditions, such as ammonia toxicity, may require additional carnitine.

As shown by the following examples, optimum results in growing catfish are obtained by addition to the diet of less than 0.2% L-carnitine, most preferably between 0.05 and 0.1% L-carnitine based on dry weight of the food. Diets containing 0.2% carnitine by dry weight of food produced less growth than 0.1% carnitine by dry weight of food (30 mg/kg fish weight). Since these results are based on diets containing 2.7% fat, optimum results using diets containing higher amounts of fat in the diet may require additional L-carnitine. The stimulation of fatty acid oxidation by L-carnitine transport of CoA-fatty acids into the mitochondria is likely to be the most important explanation of increased growth in fish fed L-carnitine. Other functions of L-carnitine such as beta oxidation of fatty acids in peroxisomes, ketone body metabolism, catabolism of branched-chained keto acids, and the release of coenzyme A to facilitate pyruvate catabolism, may also result in improved metabolic efficiency as a function of supplemental L-carnitine.

Ammonia toxicity may be reduced in catfish by the additional metabolizable energy that becomes available when carnitine facilitates oxidation of fatty acids, possibly by an increase in urea production, as observed in carnitine supplemented mice when experiencing acute ammonia toxicity.

Fish feeds are generally formulated to be either supplemental, in cases where fish receive substantial nutrition from environmental sources, or complete, in cases where fish are raised or maintained in artificial environments or high stocking densities as in commercial food fish culture. L-carnitine supplementation has the greatest effect when added to complete fish feeds.

The major portion of complete fish feeds is made up of a combination of protein supplements, often including soybean meal, fish meal, peanut meal, cottonseed, meat and bone meal, or meat meal. The channel catfish diets where carnitine would be used would have Kjeldahl nitrogen analyses indicating protein levels of between 25 and 37% for food sized fish, 32 and 46% for fingerlings, and 24 to 31% for fish over 1.3 kg used as brood fish. Grains, such as corn or wheat, as well as various grain by-products, are usually included in diet formulations as an energy source and to arrive at the overall desired protein content. Other by-products, such as distillers dried solubles and dried whey, may be included as sources of vitamins, minerals and proteins. The energy content is increased by addition of fat. Supplemental vitamins, especially ascorbic acid, minerals and trace minerals, are also added to meet the fish's requirements. Antimicrobials are also sometimes added. Antibiotics registered for use with fish for consumption are oxytetracycline and potentiated sulfonamide (18.75% sulfadimethoxine and 3.75% ormetoprin). Other antibiotics include sulfamerazine, erythromycin, kanamycin, and oxolinic acid.

As described by H. Randall Robinette, Chapter 7. "Feed Formulation and Processing", *Nutrition and Feeding of Channel Catfish (Revised)*, Southern Cooperative Series Bulletin No. 296, pp. 29-33 (February 1984), the primary feedstuffs for catfish food are fish meal, soybean meal, corn, wheat, rice bran, dicalcium phosphate and fat. Other ingredients which have been used include meat and bone meal, peanut meal, and rice mill feed. These materials are formulated to provide the necessary protein levels and digestibility while taking into consideration manufacturing concerns. An example of such a formulation, shown on page 32 in Table 3, of *Nutrition and Feeding of Channel Catfish*, is as follows:

TABLE 1

Catfish Feed Formulations Containing 32% Protein Suitable for Pelleting or Extruding.

| Ingredient | lb/ton | lb/ton |
| --- | --- | --- |
| menhaden fish meal | 160 | — |
| meat and bone meal | — | 300 |
| soybean meal, 48% protein | 965 | — |
| soybean meal, 44% protein | — | 950 |
| corn | 582 | 660 |
| rice bran or wheat shorts | 200 | — |
| wheat middlings | — | 35 |
| dicalcium phosphate | 20 | 5 |
| whey, dried | — | 48 |
| pellet binder* | 40 | — |
| fat (sprayed on feed) | 30 | — |
| trace mineral mix of Mn, Zn, Fe, Cu, I, and Co | 1 | 1 |
| vitamin mix | 1 | 1 |
| coated ascorbic acid | 0.75 | 0.75 |

*Binders are not required in manufacture by extrusion.

Catfish are generally fed manually by broadcasting feed across the surface of the water, or automatically from mechanical feeders. Most catfish are fed once per day and fed as much as they will eat. Consumption varies according to water temperature, fish size and stress. Feed rates for fish are based on a percentage of their body weight or the percentage of the standing crop weight. Feeding rates are most affected by fish size and water temperature. Particle size is also determined by the size of the fish and the water temperature, with particles ranging in size from 420 microns for fry to 3.36 mm for fish six inches or longer. Diets containing L-carnitine may be fed in the same manner as conventional feeds. Most fish feeds are either meals, high density pellets, or low density pellets. Other forms include moist pastes and slurries, flakes and crumbled pellets. Feeds are usually prepared by uniformly mixing the ingredients, including the L-carnitine, and then either extruding or pelleting the mix. Extruded feeds float. Pelleted feeds sink. In both processes, the ingredients, with the exception of labile additives, are mixed until the small particles are evenly dispersed throughout the material. Small particle sizes increase surface area and improves gelatinization and compressibility. The extruder uses a higher temperature and pressure to entrap air within the extruded feed. The pellets are dried and oil, with or without fat soluble vitamins, is sprayed onto the feed. Because carnitine is heat stable, decomposing at 197° C., it may be added before extrusion.

L-carnitine supplementation can be achieved by one of two methods: selection of materials containing high amounts of L-carnitine or addition of synthetic or purified L-carnitine to the feed. As used herein, "carnitine supplementation" refers to an increase in L-carnitine to the diet, based on percentage of dry weight of the diet. Natural materials have varying amounts of L-carnitine. Plant material has small amounts. For example, levels of L-carnitine range from 7-14 $\mu g/g$ in wheat to 20 $\mu g/g$ in alfalfa to 1.0 $\mu g/g$ in peanut, Fraenkel, G., *Distribution of Carnitine*, 2(3), 1-3 (Advanced Research Press, Inc. Cavis, Calif. 1987). Fish muscle contains 700 $\mu g/g$, Fraenkel, *The Biol. Bull.* 104, 359-71, so 6% dietary fish meal could be used to provide 0.004% L-carnitine. L-carnitine is also contained in beef muscle (640 $\mu g/g$) and sheep muscle (2,100 $\mu g/g$). Leibovitz, *Carnitine Nutrition Update* 2(3), 1-3. In general, depending on the composition, fish feed formulations containing between 5 to 15% animal products will contain less than 0.005% L-carnitine, with feeds containing lower amounts of animal products containing lower levels of L-carnitine.

Supplementation according to the method of the present invention can also be achieved by addition of L-carnitine purchased, for example, from Lonza Inc., Fair Lawn, N.J. L-carnitine is added to the diet such that it is distributed uniformly throughout the mixture of ingredients prior to extrusion or pelleting. As described above, this is most easily accomplished by thoroughly premixing the L-carnitine with a portion of one of the other ingredients, such as soybean meal or finely ground corn, prior to its being added to the bulk of the other ingredients.

Water stability of the feed particle is important to the retention of soluble nutrients, such as L-carnitine. Water stability is increased by adding binders, using finely ground ingredients, increasing the heat of pelleting to gel starch components and lowering the amounts of poor pelleting ingredients such as oil, rice bran, or wheat bran. It is important to minimize the solubility of L-carnitine in the feed so as to reduce the amount lost by leaching into the water and thereby minimize the amount required to produce the maximum weight gain. In addition to the methods described above, the L-carnitine can also be microencapsulated or acetylated to decrease its solubility prior to addition to the feed. Methods for microencapsulation are well known to those skilled in the art. Other forms in which the L-carnitine can be provided which have reduced solubility include L-tartrate carnitine, L-carnitine chloride, L-carnitine magnesium citrate, L-carnitine acetyl-HCl, L-carnitine propionyl-HCl, and L-carnitine palmitoyl-HCl.

The growth enhancing effect of L-carnitine supplementation requires the presence of a complete amino acid profile in the diet. The amino acid requirements for various species of fish are shown in Table 3 on page 4 of *Nutrient Requirements of Warmwater Fishes and Shellfishes*. The amino acids can be provided by selection of material containing the necessary amino acids or by supplementation with synthetic or purified amino acids.

The present invention will be further understood with reference to the following non-limiting examples.

EXAMPLE 1

Supplementation of Pelletized Catfish Diet With L-carnitine to Increase Growth Rates Fish and Standard Diet and Culture Conditions: Catfish, an omnivorous fish that is adapted only to fresh water and grows optimally at a temperature of 30° C., was used in the following studies. Unlike carnivorous fish, such as sea bass, which have gastric glands that secrete hydrochloric acid and pepsinogen to facilitate the digestion of large protein molecules, and which have a pyloric caeca at the anterior end of the intestine to aid in the digestion and absorption of fats, catfish can efficiently digest plant material such as corn and soybean meal, and are therefore fed diets especially formulated for catfish. Nutrient requirements, which vary in type and amounts by age, species, reproductive stage and environmental conditions, are outlined, for example, in "Nutrition and Feeding of Channel Catfish", edited by R. R. Stickney and R. T. Lovell, published in 1977 by the Nutritional Subcommitee of USDA Regional Research Project S-83 as Southern Cooperative Series Bulletin 218.

Method: A commercial diet formulated to produce a low density floating pellet was used as the basal diet. This basal diet was ground and enriched with additional vitamin premix (Table 1), ascorbic acid (300 mg/kg), and binder (20 g/kg). L-carnitine (Lonza, Inc., Fair Lawn, N.J.) was mixed into the premix at 0, 0.05, 0.1, and 0.2 percent w/w. Water was added to 10 percent immediately prior to pelletizing. 5 mm×8 mm pelleted diets were formed with a bench top pellet machine (California Pellet Mill Co., San Francisco, Calif.). After pelleting, the diets were dried with forced air to 8 per cent moisture. Diets were kept refrigerated at 10° C. until fed.

TABLE 2

| Diet composition | |
|---|---|
| Diet Component | Percentage |
| Crude protein | 35.0 |
| Fat | 2.7 |
| Crude fiber | 6.4 |
| Ash | 9.9 |
| Vitamin Mix Composition | Per kilogram premix |
| Vitamin A | 1,760,000 USP Units |
| Vitamin D-3 | 176,000 IC Units |
| Vitamin E | 6,600 IU |
| Vitamin K (MPB) | 4,840 mg |
| D-pantothenate | 8,800 mg |
| Niacin | 8,800 mg |
| Riboflavin | 1,760 mg |
| Choline chloride | 176 g |
| Vitamin B-12 | 8,800 mcg |
| Selenium (Sodium selenite) | 40.4 mg |
| (Balanced to kg with rice mill byproducts) | |

Sibling catfish fingerlings (12.2±0.2 g) with identical nutritional history were stocked 25 per 115 liter tank. Continuous flow was maintained at 1 liter per minute. The water supply was derived from a well and heated to 28° C.±2° before introduction to the culture system. The fish were fed the basal diet with no added carnitine for a two week conditioning period during which they became accustomed to the culture environment. Four replicate tanks of each of the four treatments were maintained. Diets were fed at 3 per cent of the weight of the faster growing treatment in order not to restrict the amount of feed offered to the fish. Feeding was adjusted after each two week sampling period to account for fish growth increase. The final sampling was made 12 weeks into the study after the fish had increased in weight 6 fold.

Dietary carnitine was determined with gas chromatographic methods by the Clinical Nutrition Center, University of Wisconsin, Madison, Wis. Duplicate samples of 10 g of each diet were analyzed.

Results: The fish in all treatments grew well during the study. No significant mortality was experienced in any of the tanks. The average daily gains for the 0, 0.5, 0.1, and 0.2% added carnitine treatments were 0.69, 0.74, 0.73, and 0.72 g/day respectively. A bacterial infection was noticed in two tanks during the eighth week and all tanks were treated with 40 mg Terramycin/L. for 4 hr and again after 2 days for 3 hours to halt the progress of the disease.

Feed was added to each tank on a twice daily basis with the exception of sampling days when no feed was fed. In total 2207.4 g of diet was fed into each tank during the study. Feed conversions for the 0 to 0.2% treatments were 0.66, 0.71, 0.70, and 0.69 grams of fish per grams of feed respectively.

Analysis of diets for total carnitine showed that no significant loss occurred in diets stored for one month at 10° C. Pellets containing 0.05, 0.1, and 0.2% L-carnitine and suspended in water for five minutes retained 95, 68, and 87% of the original L-carnitine respectively. The fish in this study consumed the ration in less than five minutes.

The percent relative gain by catfish fed additional L-carnitine consistently exceeded the control fish fed the basal diet. After 12 weeks, the diet with 0.1% L-carnitine showed the highest relative gain (453%), 15.6% above the gain experienced by control fish (392%), and significantly different (P<0.05). Both the 0.05 and 0.2 percent diets out-performed the control with relative gains of 426% (8.6% greater than control) and 415% (5.9% greater than control), respectively.

EXAMPLE 2

Effect of Supplementation of Pelletized Catfish Diet With L-carnitine on Total Body and Muscle Fat Preliminary analyses of total body fat and muscle fat in fish fed a diet with 7 kcal/gm protein with and without supplemental carnitine show that whole body fat as a percentage of wet weight are 9.8 for the control (no added carnitine), 9.9 for fish fed 0.05% added carnitine, 9.6 for 0.1% added carnitine, and 9.5 for 0.2% added carnitine. These results were obtained from groups of eight fish. No reduction in muscle fat was observed at this level of kcal/gm protein, although muscle fat is already very low in healthy fish, ranging from 1.7 to 1.9 for control and carnitine supplemented fish. Decreasing the visceral fat increases the efficiency of dress out for the fish. These results show that addition of L-carnitine to catfish diets in the range of 0.1 to 0.2% of the dry diet results in a decrease in total body fat of 2% and 3%, respectively.

These results were somewhat surprising in view of reports that cool water fish are not able to utilize fats that are highly saturated, such as beef tallow or some types of plant waxes, but perform more optimally when unsaturated fats such as fish oils are used in the diet, which could lead one to believe that catfish, because they are adapted metabolically to a larger variety and quantity of fats, might not be expected to require carnitine to facilitate lipid metabolism.

Fat reduction may be related to reductions in abdominal or muscle fat. The digestible energy concentration in these diets was 3011 cal/kg diet and the digestible energy to protein ratio was 8.7 kcal/gram of protein. Higher energy concentrations or larger energy to protein ratios are expected to increase fat accumulation and result in larger differences between growth and fat deposition for fish fed additional L-carnitine as compared to fish not fed additional L-carnitine.

EXAMPLE 3

Effect of Supplementation of Pelletized Catfish Diet With L-carnitine on Resistance to Ammonia Toxicity When the ammonia concentration of the culture water is elevated to chronically toxic levels (between 0.03 and 0.06 mg/l) as un-ionized ammonia, catfish growth and survival increases when fed a commercial catfish diet supplemented with L-carnitine. After six weeks, relative gain increases 10.2% when 0.1% L-carnitine is added to the diet. At 0.2% additional L-carnitine, a 6.4% increase in relative gain can be achieved. The average survival of multiple study groups exposed to chronically toxic ammonia concentrations was better when the catfish were fed a diet supplemented in L-carnitine. Without supplemental carnitine, 85% of the fish survived more than six weeks. With 0.1% L-carnitine supplementation, 100% survived. With 0.2% L-carnitine, 95% survived.

These results were unexpected. The response of channel catfish to ammonia toxicity may be different than for mammals or salt water fish. Mammals excrete mostly urea while fish excrete primarily urea. Salt water fish excrete over 90% of waste nitrogen as ammonia through the gills. Fresh water fish excrete up to 56% of waste nitrogen as ammonia and the rest as urea, creatine, creatinine, or simple amino acids. These differences would lead one to expect only an insignificant response to additional carnitine, based on comparisions with uarea excretion by mice, in contradiction to the results shown above.

Modifications and variations of the present invention, diet compositions and methods for formulation and administration thereof to fish will be obvious to those skilled in the art from the foregoing detailed description. Such modifications and variations are intended to come within the scope of the amended claims.

We claim:

1. A composition comprising catfish feed containing
   (a) L-carnitine, in a form delivering to the catfish between approximately 3 mg and 90 mg L-carnitine per kilogram catfish per day, and
   (b) between 25 and 37% protein for food sized fish, between 32 and 46% protein for fingerlings, and between 24 to 31% protein for fish over 1.3 kg used as brood fish, having between 7 and 8.7 kcal of digestible energy/gram of protein.

2. The composition of claim 1 comprising between approximately 0.01% and 0.3 weight % L-carnitine.

3. The composition of claim 1 for a channel catfish diet having Kjeldahl nitrogen analysis indicating protein levels of between 32 and 36% protein.

4. The composition of claim 1 further comprising binders and encapsulating agents to decrease solubility of the L-carnitine in the feed composition.

5. The composition of claim 1 in pelleted form.

6. The composition of claim 1 in extruded form.

7. The composition of claim 1 wherein the L-carnitine is microencapsulated.

8. The composition of claim 1 wherein the L-carnitine is in a form selected from the group consisting of acetylated L-carnitine, L-tartrate carnitine, L-carnitine chloride, L-carnitine magnesium citrate, L-carnitine acetyl-HCl, L-carnitine propionyl-HCl, and L-carnitine palmitoyl-HCl.

9. A method for increasing the growth of catfish comprising providing a catfish feed composition in a form delivering to the catfish between approximately 3 mg L-carnitine per kilogram catfish per day and 90 mg L-carnitine per kilogram catfish per day, wherien the carnitine consists essentially of L-carnitine.

10. The method of claim 9 wherein the feed contains between approximately 0.01 and 0.3 percent L-carnitine based on dry weight of the feed.

11. The method of claim 9 further comprising preparing the feed composition by mixing dry materials with moisture and the L-carnitine and extruding the mixture.

12. The method of claim 9 further comprising preparing the feed composition by mixing the dry materials with the L-carnitine and pelleting the mixture.

13. The method of claim 9 further comprising encapsulating the L-carnitine in the feed composition to decrease the solubility in water.

14. The method of claim 9 further comprising preparing the feed composition using a form of L-carnitine having decreased solubility in water.

15. The method of claim 14 wherein the L-carnitine is in a form selected from the group consisting of acetylated L-carnitine, L-tartrate carnitine, L-carnitine chloride, L-carnitine magnesium citrate, L-carnitine acetyl-HCl, L-carnitine propionyl-HCl, and L-carnitine palmitoyl-HCl.

16. The method of claim 9 further comprising providing different amounts of L-carnitine to a particular size and species of fish, measuring the increase in growth of each fish provided with a different amount of L-carnitine, and preparing a diet providing an amount of L-carnitine effective for producing an increase in growth in fish.

17. The method of claim 9 further comprising providing different amounts of L-carnitine to a particular size and species of fish, measuring the fat content of the visceral and muscle tissues of each fish provided with a different amount of L-carnitine, and preparing a diet providing an amount of L-carnitine effective in altering the fat content of the visceral and muscle tissues in fish.

18. The method of claim 9 further comprising providing different amounts of L-carnitine to a particular size and species of fish, measuring the response to ammonia toxicity of each fish provided with a different amount of L-carnitine, and preparing a diet providing an amount of L-carnitine effective in increasing the resistance of the fish to ammonia toxicity.

19. The method of claim 9 further comprising providing different amounts of L-carnitine to a particular size and species of fish, measuring the efficiency of fat utilization for energy of each fish provided with a different amount of L-carnitine, and preparing a diet providing an amount of L-carnitine effective in increasing the efficiency of fat utilization for energy by fish.

20. The method of claim 9 wherein the fish are warm-water fish.

21. The method of claim 9 wherein the fish are catfish.

22. The method of claim 21 wherein the fish are fingerling catfish and the composition contains between 0.005 and 0.2 weight percent L-carnitine.

23. The method of claim 22 for a channel catfish diet wherein the diet is provided having Kjeldahl nitrogen analyses indicating protein levels of between 25 and 37% for food sized fish, 32 and 46% for fingerlings, and 24 to 31% for fish over 1.3 kg used as brood fish.

* * * * *